United States Patent [19]
Halskov et al.

[11] Patent Number: 5,716,648
[45] Date of Patent: Feb. 10, 1998

[54] COMPOSITIONS FOR USE IN THE REGULATION OF SUBNORMAL PH VALUES IN THE INTESTINAL TRACT AND FOR TREATMENT OF BOWEL DISEASES

[75] Inventors: Søren Halskov, Virum; Svenn Klüver Jepsen, Copenhagen, both of Denmark

[73] Assignee: Farmaceutisk Laboratorium Ferring A/S, Vanlose, Denmark

[21] Appl. No.: 556,966

[22] PCT Filed: Jun. 8, 1994

[86] PCT No.: PCT/DK94/00223

§ 371 Date: Dec. 21, 1995

§ 102(e) Date: Dec. 21, 1995

[87] PCT Pub. No.: WO94/28911

PCT Pub. Date: Dec. 22, 1994

[30] Foreign Application Priority Data

Jun. 8, 1993 [DK] Denmark ................ 0664/93

[51] Int. Cl.$^6$ .......... A61K 33/06; A61K 33/10; A61K 33/08; A61K 31/61
[52] U.S. Cl. .......... 424/682; 424/683; 424/684; 424/686; 424/688; 424/690; 424/693; 424/717; 514/65; 514/163; 514/166
[58] Field of Search ........... 424/682, 683, 424/684, 686, 688, 690, 693, 717; 514/65, 163, 166

[56] References Cited

U.S. PATENT DOCUMENTS

| | | | |
|---|---|---|---|
| Re. 33,239 | 6/1990 | Halskov | 206/213.1 |
| 4,289,750 | 9/1981 | Kopp et al. | 424/33 |
| 4,451,454 | 5/1984 | Wong | 424/127 |
| 4,496,553 | 1/1985 | Halskov | 514/166 |
| 4,632,921 | 12/1986 | Bauer | 514/163 |
| 4,744,987 | 5/1988 | Mehra et al. | 424/156 |
| 4,980,173 | 12/1990 | Halskov | 424/490 |
| 5,541,170 | 7/1996 | Rhodes et al. | 514/166 |

FOREIGN PATENT DOCUMENTS

| | | |
|---|---|---|
| 0 381 414 | 8/1990 | European Pat. Off. |
| WO83/00435 | 2/1983 | WIPO |
| WO91/04018 | 4/1991 | WIPO |
| WO92/09270 | 6/1992 | WIPO |

OTHER PUBLICATIONS

CA: 114(30125) Enteric Formulations of Physiologically--Active Peptides and Proteins (1990) [Abstract Enclosed].
Fass (1992), Farmacevtiska specialiteter i Sverige, Förtechning över humanläkemedel, p. 622.
Fallingborg, J. et al, Aliment. Pharmacol. Therap. 3, 605–613 (1989).
United States Pharmacopoeia XXII NF XVII, 1990.
Fallingborg, J. et al, "Gastrointestinal pH–Profiles In Patients With Active Ulcerative Colitis"—Symposium IBD and Salicylates, Paris, Dec. 10–11, 1992.
Svartz, N., Acta Med. Scand. 110, 577–596 (1942).
Klotz, U., Clin. Pharmacokinet. 10, 285–302 (1985).
Hanauer, S.B., Scand. J. Gastroenterol. 25, suppl. 175, 97–106 (1990).
Lauterburg, B.H. et al, "Inflammatory Bowel Disease: Current Status and Future Approach", editor R. P. MacDermott, Elsevier Science Publisher B.V., 273–277 (1988).
Fischer–Nielsen et al, Free Radical Biology & Medicine, 13, 121–126 (1992).
Ahnfelt–Rønne et al, Gastroenterol. 98, 1162–1169 (1990).
Palsmeier, R.T. et al, Pharm. Res. 9, 933–938 (1992).
Roediger et al, Biochem. Pharmacol. 35(2), 221–225 (1986).
Roediger et al, Pharmacology 39, 39–45 (1989).

*Primary Examiner*—Kevin E. Weddington
*Attorney, Agent, or Firm*—Holman & Stern, PLLC

[57] ABSTRACT

Compositions for use in the regulation of subnormal pH values in intestinal tract and for treatment of bowel diseases. The compositions comprise a coating and a substantially insoluble alkaline material confined within said coating, the composition being adapted so as to ensure the availability of an amount of said pH regulating alkaline material in the lumen of the gastrointestinal tract exhibiting subnormal pH values. E.g. In the proximal small intestine, the mid small intestine, the distal small intestine, the caecum, the ascending colon, the transverse colon, the descending colon, the sigmoid colon and/or the rectum. The compositions may also comprise a medicament for treatment of bowel disease, e.g. 5-aminosalicylic acid for the treatment of Crohn's disease and colitis ulcerosa. The administration may be oral composition or enemas or suppositories.

38 Claims, No Drawings

COMPOSITIONS FOR USE IN THE REGULATION OF SUBNORMAL PH VALUES IN THE INTESTINAL TRACT AND FOR TREATMENT OF BOWEL DISEASES

This application is a 371 of PCT/DK94/00223 filed Jun. 8, 1994.

FIELD OF THE INVENTION

The present invention provides compositions for oral or rectal administration having pH-regulating effect, in particular for raising a subnormal pH in the intestine to a pH close to the pH usually found in the intestine, and/or the use of a composition in the treatment of bowel diseases e.g. inflammatory bowel diseases and/or for obtaining ulcer healing in the intestine.

In particular, the composition according to the invention optionally contains an active medicament for the treatment of Crohn's disease or colitis ulcerosa, e.g. 5-aminosalicylic acid (5-ASA).

BRIEF DISCLOSURE OF THE INVENTION

In one of its broadest aspects, the invention provides a composition for oral administration, said composition comprising:

a physiologically acceptable coating, and a physiologically acceptable pH regulating alkaline material confined within said coating, said pH regulating alkaline material being substantially insoluble (as defined herein), the nature and the amount of said coating and of said pH regulating alkaline material being adapted so as to ensure the availability of an amount of said pH regulating alkaline material in the lumen of a target part of the gastrointestinal tract from the proximal small intestine to rectum, said target part exhibiting a pH below the pH normally found in said target part, and to ensure a raise in the pH in said lumen to a pH which is close to the pH normally found in said target part.

The target part may be a part which by one or more intraluminal pH-measurements has shown pH values below the pH value normally found in said target part.

An aspect of the invention is a composition which is adapted to raise the pH to a pH within the 5–95 percentiles of the normal pH values in said target part of the gastrointestinal tract.

According to a main aspect of the invention, the target part exhibiting a pH below the pH normally found is the proximal small intestine, the mid small intestine, the distal small intestine, the caecum, the ascending colon, the transverse colon, the descending colon, the sigmoid colon and/or the rectum.

The invention provides a composition for oral administration, the composition comprising a coating which enables the pH regulating alkaline material to pass through the ventricle substantially without being affected by the gastric juices.

THE IMPORTANT ASPECTS OF THE INVENTION

The particular advantages of the composition and use according to the invention are that a specific pH adjustment which is targeted to the individual parts of the intestine has been made possible.

The localized pH adjustments according to the invention can be related to the varying pH values prevailing in the various parts of the intestines.

It has been found that in normal subjects the pH values varies considerably in different parts of the gastrointestinal tract. Fallingborg et al., (Ailment. Pharmacol. Therap. 3, 605–613 (1989)) used a pH sensitive radiotransmitting capsule for pH determinations in the intestinal lumen of various parts of the intestinal tract. The location of the capsule was determined by X-ray.

In all subjects pH values below 3 were found in the stomach. When the capsule entered the duodenum a sharp rise occurred, and the pH reached a median value of 6.4. The pH level gradually increased down the small intestine.

The median values were: 6.6 in the proximal part, 7.0 in the mid part, and 7.3 in the distal part of the small intestine. In 17 subjects pH decreased gradually by 0.1–0.8 pH units during the last hours the capsules stayed in the distal part of the small intestine, but the pH did not fall below 6.3.

When the capsule reached the caecum, the pH dropped from 0.5 to 2.5 pH units to a median value of 5.7. The pH levels of the ascending colon and the transverse colon were almost identical to that of the caecum (5,6 in the ascending and 5.7 in the transverse colon), but the pH rose in the descending colon (6,6), and in the sigmoid colon and rectum (6,6). The median faecal pH was 6.5.

The present invention relates to the adjustment of LOW pH values in the intestine, i.e. raising subnormal pH values to values within a more physiologically appropriate range.

The compositions according to the invention provide the targeted deposition in the intestine of alkaline material capable of neutralizing the acid material present in the intestinal lumen in individuals suffering from localized pH distortions.

In various functional distortions of living cells/organs the maintenance of a normal physiological pH value is jeopardized. In order to alleviate or cure such intestinal distortions, the compositions of the present invention may be administered in appropriate dosage forms, individually adapted to the severity of the distortions of the pH profile.

The pH regulating alkaline material of the composition according the present invention is confined within a coating which enables the pH regulating alkaline material to pass through the ventricle substantially without being affected by the gastric juices. The coating is preferably an enterocoating, in particular a coating which is insoluble in gastric juice of pH below 4 and soluble in intestinal juice exhibiting a pH from 4 to 7. In a preferred embodiment the coating is Eudragit L12,5 P.

A main aspect of the invention is a composition wherein the pH regulating alkaline material is an acid soluble salt.

In the present context, the term "substantially insoluble" is to be understood as comprising the following descriptive terms (cf. the United States Pharmacopoeia XXII NF XVII, 1990) designating the ratio between:

Parts of solvent required for 1 part of solute,
i.e. Parts of water required for 1 part of pH regulating alkaline material

| Descriptive Term | Ratio |
| --- | --- |
| SLIGHTLY SOLUBLE | From 100 to 1000 |
| VERY SLIGHTLY SOLUBLE | From 1000 to 10,000 |
| PRACTICALLY INSOLUBLE, OR INSOLUBLE | 10,000 and over |

The compositions according to the invention comprise a pH regulating alkaline material being substantially insoluble according to the above definitions. Said pH regulating alkaline materials are—according to the invention—selected so as to ensure that the material is substantially insoluble in intestinal fluids exhibiting a pH normally found in the target part of the intestinal lumen in question.

In particular the pH regulating alkaline materials are insoluble in intestinal fluids exhibiting an alkaline pH or a pH slightly below or around neutral. However, the pH regulating alkaline materials are increasingly soluble in intestinal fluids of a decreasing pH, thereby causing neutralization of some of the acid materials present in the lumen of a target part of the gastrointestinal tract exhibiting a pH below the pH normally found in said target part.

In a preferred embodiment the composition for oral administration comprises:

a physiologically acceptable coating, and a physiologically acceptable pH regulating material confined within said coating, said pH regulating material being substantially insoluble in intestinal fluids having a neutral pH or a pH in the range of about 6–8, and being rather soluble in intestinal fluids having an acid pH, and when solubilized giving rise to proton acceptors, the nature and the amount of said coating and of said pH regulating material being adapted so as to ensure the availability of an amount of proton acceptors in the lumen of a target part of the gastrointestinal tract from the proximal small intestine to rectum, said target part of the gastrointestinal tract exhibiting a pH below the pH normally found in said target part, and to ensure a raise in the pH in said lumen to a pH which is close to the pH normally found in said target part.

Preferably the pH regulating alkaline material is soluble in intestinal fluids at a pH below about 5. The pH regulating alkaline material is preferably selected from the group consisting of substantially insoluble carbonates, bicarbonates, silicates, hydroxides and phosphates, preferably of alkaline earth metals, more preferably magnesium or calcium, most preferably calcium.

The pH regulating alkaline material is preferably an acid soluble salt. In a preferred embodiment the pH regulating alkaline material is calcium carbonate.

The unit dosage of alkaline material depends on the acidity to be neutralized, and may range from 1 mmol to 1 mol, preferably from 5 mmol to 100 mmol, optionally administered 2–8 times, such as 4–6 times per day. If appropriate, the compositions may be administered in between meals, in certain cases in a fasting state. The administration may be used in acute cases and as a maintenance treatment.

The pH raise may be more than ½ unit, optionally 1 or 2 pH units.

In a preferred embodiment the composition administered per day is capable of neutralizing from 1–100 milliequivalents acid, preferably 10–60 milliequivalents acid.

The pH regulating alkaline material is preferably in the form of a coated granulate.

Furthermore, another overall aspect of the invention is the administration of the compositions according to the invention to individuals suffering from various functional disorders in the bowel, e.g. inflammation of the bowel. These individuals may exhibit distorted pH profiles possibly due to cell decomposition in the area, including decomposition of the cells attracted to the area as a part of an inflammatory reaction. This may particularly relate to invasive bowel disease, e.g. ulcerative invasive bowel diseases.

As an example of an inflammatory bowel disease where a distorted pH profile has been observed, reference is made to the poster presented by Fallingborg et al., entitled "Gastrointestinal pH-profiles in patients with active ulcerative colitis" at the Symposion "IBD and Salicylates", Paris, 10.–11. December 1992. The poster reported pH measurements on 6 patients with ulcerative pancolitis. Normal pH levels were found in the stomach and the small intestine of all six patients, and in three patients the pH values in the colon were also normal. However, in the three remaining patients very low pH levels were found in the colon. The lowest measured pH values were 2.3, 2.9, and 3.4. These three patients also had the highest disease activity. As compared to the normal median pH-value of 5.7 in the colon these values represent a significant drop.

Based on the above findings it can be assumed that other bowel diseases may give raise to distorted pH profiles including subnormal pH levels, in particular Crohn's disease, colitis ulcerosa or an unclassifiable form of said diseases.

Other diseases include—if the hypothesis is correct—bowel diseases which are microbially induced, e.g. by bacteria such as Salmonella, Campylobacter, Shigella, *E. Coli*, *Clostridium difficile*, or parasites such as *Entamoeba histolytica*, or vira such as Parvovirus. Also, the bowel disease may be a medicamentally induced bowel disease, e.g. induced by a non-steroid anti-inflammatory drug (NSAID).

Accordingly, the present invention provides a composition wherein the intestinal target part exhibiting a pH below the normal pH is the site of a disease afflicting the bowel such as an invasive bowel disease, in particular an inflammatory bowel disease.

Accordingly, the invention relates to a composition for the treatment of bowel diseases by oral administration comprising:

a first physiologically acceptable coating, and a physiologically acceptable pH regulating alkaline material confined within said first coating, said pH regulating alkaline material being substantially insoluble (as defined herein), the nature and the amount of said coating and of said pH regulating alkaline material being adapted so as to ensure the availability of an amount of said pH regulating alkaline material in the lumen of a target part of the gastrointestinal tract from the proximal small intestine to rectum, said target part exhibiting a pH below the pH normally found in said target part and to ensure a raise in the pH in said lumen to a pH which is close to the pH normally found in said target part, a second physiologically acceptable coating, and an ingredient confined within said second coating, said ingredient being therapeutically active against said bowel disease.

Thus, the composition according to the invention comprises a physiologically acceptable base capable of raising the pH-value in an afflicted site to a suitable level and optionally an active medicament, the base and the medicament, if any, being provided with a coating to ensure that the medicament and the base are not released until at the site where the contemplated effect is desired.

In a preferred embodiment the composition according to the invention is a composition wherein the coated pH regulating alkaline material and the coated active ingredient are each formulated as granulates.

In another embodiment the composition according to the invention is a composition wherein the granulates are filled into a physiologically acceptable capsule. Alternatively, the granulates might be suspended in an orally administrable liquid.

In a main aspect of the invention the composition according to the invention is a composition wherein the active ingredient is a medicament which is selected from

- an antiinflammatory medicament, e.g. 5-aminosalicylic acid, 4-aminosalicylic acid, glucocorticoids such as prednisolone for systemic or topic administration;
- a membrane stabilizing medicament such as disodium-cromoglycate;
- an immunomodulating/immunosuppressive medicament such as ciclosporin, fucidin, FK506, azathioprine, or 6-mercaptopurine;
- a cytoprotective or mucosal protective agent such as sucralfate, or bismuth subcitrate; and
- a cytostatic agent such as methotrexate.

Thus, important compositions are compositions wherein the active ingredient is a medicament for treatment of an inflammatory bowel disease. In particular the inflammatory bowel disease is Crohn's disease, colitis ulcerosa or an unclassified form of said diseases.

The composition may include—as the active ingredient—a medicament for treatment of microbially induced bowel diseases, e.g. induce by bacteria such as Salmonella, Campylobacter, Shigella, *E. Coli*, *Clostridium difficile*, or parasites such as *Entamoeba histolytica*, or vira such as Parvovirus.

Especially preferred is 5-aminosalicylic acid or a physiologically acceptable salt or ester thereof as the active ingredient.

Yet another main aspect according to the invention is a composition for rectal or enteral administration comprising:

- a physiologically acceptable carrier and
- a physiologically acceptable pH regulating alkaline material said pH regulating alkaline material being substantially insoluble (as herein defined), the nature and the amount of said carrier and of said pH regulating alkaline material being adapted so as to ensure the availability of an amount of said pH regulating alkaline material in the lumen of a target part of the colon and/or the rectum. said target part exhibiting a pH below the pH normally found in said target part, and to ensure a raise in the pH in said lumen to a pH which is close to the pH normally found in said target part.

The said composition may be formulated as an enema or as suppositories. The target part is the site of a disease afflicting the lower bowel, e.g. proctitis, proctosigmoiditis and/or distal colitis.

The invention further comprise the use of a composition comprising a pH regulating alkaline material for the production of a medicament for treatment of individuals exhibiting a subnormal pH in the proximal small intestine, the distal small intestine, the caecum, the ascending colon, the transverse colon, the descending colon, the sigmoid colon and/or the rectum.

The subnormal pH has optionally been determined by an intraluminal pH measurement.

In a preferred embodiment, the invention relates to the use of a composition comprising a therapeutically active ingredient and a pH regulating alkaline material for the production of a medicament for the treatment of individuals suffering from a bowel disease and exhibiting a subnormal pH in the proximal small intestine, the mid small intestine, the distal small intestine, the caecum, the ascending colon, the transverse colon, the descending colon, the sigmoid colon and/or the rectum.

In a still further aspect, the invention relates to a method for the treatment of individuals exhibiting a subnormal pH in a target part of the proximal small intestine, the distal small intestine, the caecum, the ascending colon, the transverse colon, the descending colon, the sigmoid colon and/or the rectum, which method comprises administering a pH regulating alkaline material in a sufficient amount to ensure a raise in the pH in said target part to a pH close to the pH normally found in said target part.

In a preferred embodiment, the invention relates to a method for adjusting the pH and optionally treating bowel diseases locally in a target part of the gastrointestinal tract comprising the proximal small intestine, the mid small intestine, the distal small intestine, the caecum, the ascending colon, the transverse colon, the descending colon, the sigmoid colon and/or the rectum from a pH value below the normal pH value to a pH value closer to said normal pH value, which method comprises

- measuring the intraluminal pH in said target part, and
- administering a composition comprising an pH regulating alkaline material as defined above,
- and optionally a medicament for treatment of the bowel disease.

The intraluminal pH measurements may be made various methods known in the art, e.g. by means of a radiotelemetry device as described by Fallingborg et al., op. cit.. Alternatively, methods based on breath analysis may be used, or pH measuring electrode devices, or methods involving placing probes provided with colour indicators in the gastrointestinal tract, or other systems for intraluminal measurements.

The aspect of combining a targeted pH regulation and a specific medication will now be further described with respect to a preferred embodiment.

BACKGROUND OF A PREFERRED EMBODIMENT ACCORDING TO THE INVENTION

A main aspect of the invention relates to compositions for the treatment of Crohn's disease, colitis ulcerosa or an unclassifiable form of said diseases.

Crohn's disease and colitis ulcerosa are two diseases with partially unknown etiology. These diseases to some extent have the same symptoms, and have much in common as regards possible methods of treatment. It was a breakthrough in the treatment of inflammatory bowel diseases when at one time it turned out that the compound sulphasalazine, which originally was synthesized in order to combine an antibiotic and an anti-inflammatory for use in the connective tissue of the joints in patients with rheumatoid arthritis, was also active against colitis ulcerosa (N. Svartz, Acta Med. Scand. 110, 577–596 (1942). It has turned out that the effect is due to the fact that sulphasalazine with the formula

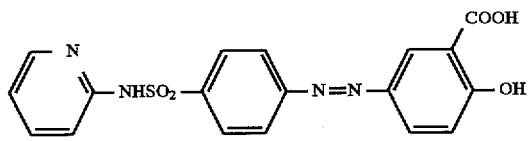

in the organism undergoes cleavage around the azo-bond, thereby forming sulphapyridine having the formula

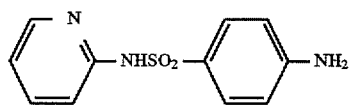

and mesalazine (5-aminosalicylic acid; 5-ASA) having the formula

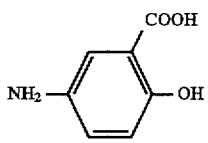

sulphapyridine apparently acting as carrier for 5-ASA which is the active moiety of sulphasalazine in connection with inflammatory bowel diseases (U. Klotz, Clin. Pharmacokinet. 10, 285–302 (1985)). In case of oral administration of sulphasalazine the substance reaches the colon in intact state, at which site the azo-bond is cleaved by the action of the intestinal flora, but recent years have seen the development of methods of treatment involving peroral or rectal administration of unbound 5-ASA, e.g. in the form of depot tablets (controlled release tablets) or enemas. By way of a special pharmaceutical formulation the depot tablets are produced so that the active principle 5-ASA is released slowly and continuously in both the small intestine and the colon. The preparation "Pentasa®" is an example of a 5-ASA-formulation which is available both as tablets and enema.

The oral "Pentasa®" formulation is described in the applicant's U.S. Pat. Nos. 4,496,553 and 4,980,173. The enema formulation is described in U.S. Pat. No. Re 33,239. These patents are incorporated by reference.

In U.S. Pat. No. 4,632,921 various readily soluble 5-ASA formulations are suggested, wherein 5-ASA is mixed with basic auxiliaries and/or buffer mixtures which in a 1% aqueous solution give pH values in the range from 8 to 12.

The mechanism of action of the anti-inflammatory compound 5-ASA has not yet been thoroughly elucidated. Several theories are considered, including inhibition of antibody synthesis, inhibition of the cyclooxygenase and lipoxygenase reaction pathways, lowering the activity of neutrophilic cells, suppression of fatty acid oxidation, and ability to act as scavenger for free oxygen radicals, i.e. as anti-oxidant (S. B. Hanauer, Scand. J. Gastroenterol. 25, suppl. 175, 97–106 (1990)). The latter mechanism of action is granted substantial importance for the anti-inflammatory activity of 5-ASA in vivo (Lauterburg et al. in "Inflammatory Bowel Disease: Current Status and Future Approach" edited by R. P. MacDermott, Elsevier Science Publisher B. V, page 273–277 (1988); Fischer-Nielsen et al., Free Rad. Biol. Med. 13, 121–126 (1992)), i.a. because it is documented that 5-ASA inactivates free oxygen-radicals in sulphasalazine treated patients with colitis ulcerosa (Ahnfelt-Ronne et al., Gastroenterol. 98, 1162–1169 (1990)).

Even though a topical treatment of the inflamed site with 5-ASA has helped extremely many patients suffering from an inflammatory bowel disease there are, however, still some patients who do not respond to this mode of treatment.

As described above, it was shown by Fallingborg et al. that 3 patients with severe attacks of inflammatory bowel diseases exhibited a surprisingly significant drop in pH-value in the intestine as compared with healthy test persons.

It has also turned out that the antioxidant properties of 5-ASA are fortified at higher pH-values (Fischer-Nielsen et al., Free Radical Biology & Medicine 13, 121–126 (1992)), which is probably due to the redox properties of 5-ASA being pH-dependant, so that higher pH-values augment the anti-oxidative properties of 5-ASA (R. T. Palsmeier et al., Pharm. Res. 9, 933–938 (1992)). Consequently, the in situ effect of 5-ASA will depend on the pH-value in the site, since a too low pH-value will reduce or eliminate the action of the substance. In other words, the ability of 5-ASA to act as antioxidant in vivo will be affected negatively by a low pH-value in the inflamed site.

Also other of the known mechanisms of action of 5-ASA may be affected by the pH-conditions in the intestine. This applies to the ability of 5-ASA to suppress fatty acid oxidation and to release CoA from acetyl-CoA during acetylation of 5-ASA; see Roediger et al., Biochem. Pharmacol. 35 (2), 221–225 (1986) and Roediger et al., Pharmacology 39, 39–45 (1989). The acetylation of 5-ASA increases with increasing pH, the nucleophilicity of the amino group in 5-ASA being increased.

Consequently, it is an object of the present invention to provide combination preparations, administered concomitantly or successively, comprising an active medicament and a pH-regulating compound.

The composition according to the invention contain a pH-regulating compound, for oral or rectal use in connection with colitis ulcerosa and Crohn's disease. The preparations according to the invention i.a. aim at treating such patients who due to abnormally low pH-values in the intestine cannot utilize the traditional 5-ASA-containing preparations. The composition according to the invention may enhance the effect of 5-ASA at the inflamed site.

The compositions according to the invention comprise a physiologically acceptable coating, which is—as described above—adapted to ensure the availability of the pH-regulating alkaline material in a target part of the gastrointestinal tract from the proximal small intestine to the rectum.

In practice, this requirement is met by coatings which enable the pH regulating material to pass through the ventricle substantially without being affected by the gastric juices.

The pH in gastric juice in the fasting state is normally below 3, cf. Fallingborg et al op. cit., but may raise to 4 or even higher depending on the gastric content.

Therefore a coating which is insoluble in gastric juices of pH below 4 will normally provide the necessary safety margin, provided they are soluble in intestinal juices exhibiting a higher pH, preferably from 4 to 7, more preferably from 6 to 7.

This requirement can be met by use of the so-called entero-coatings, also known as enteric coatings.

Generally, enteric coatings are those which remain intact in the stomach, but will dissolve and release the contents of the dosage form once it reaches the small intestine. The purpose of an enteric coating is to delay the release of drugs which are inactivated by the stomach contents or may cause nausea or bleeding by irritating the gastric mucosa.

The action of enteric coatings results from a difference in composition of the respective gastric and intestinal environments in regard to pH and enzymatic properties. Most currently used enteric coatings are those which remain undissociated in the low pH environment of the stomach, but readily ionize when the pH rises to about 4 or 5. The most effective enteric polymers are polyacids having a pKa of 3 to 5.

The earliest enteric coatings used formalin treated gelatin, or shellac, but the main disadvantage resulted from further polymerization that occurred on storage, often resulting in failure to release the active contents.

An applicable polymer is cellulose acetate phthalate (CAP) which is capable of functioning effectively as an enteric coating. However, a pH greater than 6 usually is required for solubility and thus a delay in release may ensue. It also is relatively permeable to moisture and gastric fluid compared to most enteric polymers. Another useful polymer is polyvinyl acetate phthalate (PVAP) which is less permeable to moisture and gastric fluid, more stable to hydrolysis and able to ionize at a lower pH, resulting in earlier release of active ingredients in the duodenum.

Another available polymer is hydroxypropyl methylcellulose phthalate (HPMCP). This has similar stability to PVAP is soluble in aqueous media having a pH greater than 5–6. A final and preferred example of currently used polymers are those based on methacrylic acid-methacrylic acid ester copolymers with acidic ionizable groups known under the common trade name "Eudragit".

Eudragit L and S are anionic copolymers of methacrylic acid and methyl methacrylate and are both used as acid resistant coatings. Eudragit L and S are dissolved at pH greater than 6 and 7, respectively. A particularly preferred coating is "Eudragit L 12,5 P".

Generally speaking, the coating for the pH-regulating material, which in case of compositions also comprising a therapeutically active ingredient against a bowel disease is denominated the "first physiologically acceptable coating", should meet the above-mentioned criteria regarding the availability of the pH-regulating alkaline material. As stated above a number of commercially available enteric coatings may be used. Compositions also comprising a therapeutically active ingredient further comprises a "second physiologically acceptable coating" for the active ingredient.

Depending on the nature of the active ingredient and the site of the target part of the intestinal tract the second coating may be the same as or preferably different from the first coating.

Again a number of commercially available coatings may be used depending on the target part of the intestinal tract, i.e. the site of the bowel disease in the individual patient.

In the presently preferred embodiment the therapeutically effective ingredient is 5-ASA, which formulated as "Pentasa" has proved to be efficient against both ulcerative colitis and Crohn's disease.

The Pentasa formulation, the general principles of which is described in U.S. Pat. No. 4,496,553 (which is incorporated by reference) contains the 5-ASA in the form of microgranules individually coated with a semipermeable membrane of ethylcellulose. This principle may advantageously be used also in the present invention, combining enteric coated alkaline material granulated with ethyl cellulose with 5-ASA in an oral composition together with usual formulation aids or excipients, e.g. fillers like microcrystalline cellulose and/or lubricants, e.g. magnesium stearate and talc (1:9).

It is also possible to formulate the preparation for rectal administration, e.g. in the form of enema, suppositories, rectal-foam or the like.

As pH-regulating substances use is made of those which are capable of raising abnormally low pH-values in the intestine (both the small and the large intestine, locally as well as over larger areas) to normal conditions.

The composition of the preparation can be stipulated within wide limits considering the contemplated use:
pH-regulating substance and optionally active medicament: 1–100%
Fillers: 0–99%
Coating: 0–99%

The following examples illustrate the invention.

EXAMPLE A

This example is an in vitro experiment designed to simulate the chemical environment in a disease afflicted part of the intestine and to investigate the change in pH associated with treatment of said part with a composition according to the invention.

A solution (solution I) is made from the following ingredients (based on the tabular summary in "Scientific Tables", Edited by K. Nielsen and C. Gleitner, published by CIBA-GEIGY Limited, Basle, Switzerland, 7. Edition, 1975, p. p. 574):
Alanine 0.7 g
Glutamine 1,4 g
Glycine 0.3 g
Leucine 0.5 g
Taurine 0.5 g
Concentrated $H_2SO_4$ (corresponding to total sulfate in serum ) 2.4 g
$H_3PO_4$ 85% (corresponding to total phosphate in serum) 0.4 g
NaOH to a pH of 3.0
Demineralized water up to 1000 ml
This solution corresponds to approx.:
30 mmol/l amino acids
25 mmol/l sulfate
4 mmol/l phosphate It should be mentioned that the concentration of free amino acids in plasma is approx. 3 mmol/kg and in leucocytes approx. 100 mmol/kg. The concentration of amino acids at 100% protein cleavage in serum is approx. 500 mmol/kg.

A dispersion (dispersion II) is then made from 1 g $CaCO_3$ in demineralized water diluted to 1000 ml. This corresponds to approx. 10 mmol/l.

Ten ml of (I) are mixed with ten ml of (II), and the pH change in the mixture is determined. The following results are found:

| Time (min.) | 0 | 1 | 3 | infinite |
|---|---|---|---|---|
| pH | 5.8 | 6.3 | 6.5 | 6.8 |

Then 10 ml of (I) are mixed with 5 ml of (II) and 5 ml of demineralized water, and the change in pH is measured as above. The following results are found:

| Time (min.) | 0 | 1 | 3 | infinite |
|---|---|---|---|---|
| pH | 4.1 | 5.4 | 6.0 | 6.5 |

Finally, 10 ml of (I) are mixed with 1 ml of (II) and 9 ml of demineralized water, and the pH measurement procedure is repeated. The following results are found:

| Time (min.) | 0 | 1 | 3 | infinite |
|---|---|---|---|---|
| pH | 3.2 | 3.3 | 3.3 | 3.3 |

It is seen that 5 ml of (II) lead to almost the same rise in pH as 10 ml of (II), whereas 1 ml of (II) has only negligible effect.

EXAMPLE B

In a further in vitro experiment designed to simulate the environment in a lumen of a part of the intestinal tract exhibiting normal pH values and subnormal pH values, an "artificial faeces" without food residues was prepared.

The composition was based on the tabular summary in "Scientific Tables", CIBA-GEIGY, op. cit., p. 657–699. The pH values in adult stools are as indicated 5,85–8,45.

Composition:
I. Bicarbonate ($Ca(HCO_3)_2$) 0,40 g
   Phosphate ($NaH_2PO_4$) 2,65 g
   Lactic acid (85% sat.) 1,06 g
   Sodium acetate 1,36 g
II. NaOH ad pH 6,5
III. Demineralized water ad 127 g The constituents of I were slurried in 100 g III. pH was adjusted to 6,5 by means of II, and III was added to form 127 g of the mixture which is close to the average amount of adult stools in 24 hours.

Test 1

The artificial faeces (127 g) was mixed with 1 g $CaCO_3$ and 100 g demineralized water and stirred. The pH change of the mixture was determined. The following results were found:

| Time (minutes) | 0 | 60 | infinite |
|---|---|---|---|
| pH | 5.6 | 6.8 | 8.0 |

Test 2

The artificial faeces (127 g) was mixed with 0.5 g $CaCO_3$ and 100 g demineralized water and stirred. The pH change of the mixture was determined. The following results were found:

| Time (minutes) | 0 | 60 | infinite |
|---|---|---|---|
| pH | 5.6 | 6.2 | 7.0 |

Test 3

In order to simulate the environment in a lumen of the intestinal tract exhibiting a subnormal pH value, the pH of the above composition was lowered to 3.5 by addition of 4.6 g (43 mmol) lactic acid.

5 Doses of 1 g $CaCO_3$ were added in intervals of 1 minute. Following stirring, the pH was determined.

| | Time | pH |
|---|---|---|
| Initial | 0 min | 3.5 |
| 1 g $CaCO_3$ | 1 min | 4.2 |
| 1 g $CaCO_3$ | 1 min | 4.7 |
| 1 g $CaCO_3$ | 1 min | 4.7 |
| 1 g $CaCO_3$ | 1 min | 5.2 |
| 1 g $CaCO_3$ | 1 min | 5.6 |
| | 15 min | 6.1 |
| | 30 min | 6.4 |
| | 300 min | 7.1 |

It appears from the above results that the addition of 5 g $CaCO_3$ led to a raise in pH to within the normal range. The acid content of the original composition was about 17 mmol and the further addition of 43 mmol lactic acid lead to about 60 mmol of acid.

The added 5 g $CaCO_3$ simulates the pH regulating alkaline material as it would be available in the intestines following rupture of the enteric coating.

Based on the above result it may be assumed that a composition according to the present invention would be able to raise the pH in a lumen of the intestinal tract exhibiting a subnormal pH value close to the normal range.

The following examples describe some preferred formulations of the compositions.

EXAMPLE 1 pH-regulating granulate (entero-coated)

Use is made of the following ingredients:
Calcium carbonate 500 g
Microcrystalline cellulose 500 g
Demineralized water q.s.
Eudragit® L12,5P (coating) q.s.

The mixture of calcium carbonate and microcrystalline cellulose is granulated with water, whereafter the granulate is dried and coated.

EXAMPLE 2 pH-regulating tablet (entero-coated granulate)

For 1000 tablets the following ingredients are used:
Calcium carbonate 300 g
Microcrystalline cellulose 120 g
Demineralized water q.s.
Eudragit® L12,5P (coating) q.s.
Microcrystalline cellulose q.s.
Magnesium stearate+talc (1:9) 30 g Calcium carbonate and microcrystalline cellulose are mixed and granulated with demineralized water, whereafter the granulate is dried and coated. The coated granulate is mixed with microcrystalline cellulose (approx. 190 g), magnesium stearate and talc, and from this mixture tablets with a diameter of 13.5 mm are pressed.

EXAMPLE 3 pH-regulating tablet (entero-coated)

For 1000 tablets the following ingredients are used:
Calcium carbonate 400 g
Microcrystalline cellulose 220 g
Demineralized water q.s.
Magnesium stearate+talc (1:9) 25 g
Eudragit® L12,5P (coating) q.s.

Calcium carbonate and microcrystalline cellulose are mixed and granulated with demineralized water. The granulate is dried and mixed with magnesium stearate and talc, whereafter arched tablet cores with a diameter of 12 mm are compressed from the mixture. Finally, the cores produced are coated with Eudragit® L12,5P.

EXAMPLE 4

Combination granulate containing 5-ASA and pH-regulating substance

Two granulates A and B are produced which consist of:
A: Calcium carbonate 300 g
   Microcrystalline cellulose 150 g
   Demineralized water q.s.
   Eudragit® L12,5P (coating) q.s.
B: 5-aminosalicylic acid (5-ASA) 500 g
   isopropanol+polyvinylpyrrolidone (9:1) q.s.
   ethyl cellulose+acetone (1:20) q.s.

Granulate A is prepared by granulating calcium carbonate and microcrystalline cellulose with demineralized water. The dried granulate is coated with Eudragit® L12,5P.

Granulate B is prepared by granulating 5-ASA with the mixture of isopropanol and polyvinylpyrrolidone. After drying, the granulate is coated with the mixture of ethylcellulose and acetone. Finally the two granulates are mixed.

EXAMPLE 5

Combination tablets containing 5-ASA and pH-regulating substance

Following the procedure of example 4 two granulates A and B are produced which consist of:
A: Calcium carbonate 150 g
  Microcrystalline cellulose 60 g
  Demineralized water q.s.
  Eudragit® L12,5P (coating) q.s.
B: 5-aminosalicylic acid (5-ASA) 250 g
  isopropanol+polyvinylpyrrolidone (9:1) q.s.
  ethyl cellulose+acetone (1:20) q.s.

The coated granulates A and B produced are mixed with 30 g magnesium stearate/talc and 200 g microcrystalline cellulose, and 1000 tablets with a diameter of 13,5 mm are pressed from the resulting mixture.

EXAMPLE 6

SUPPOSITORIES

Microcrystalline cellulose 500 mg
$CaCO_3$ 500 mg
Magnesium stearate 75 mg
Macrogol 6000 425 mg are compressed to form suppositories.

EXAMPLE 7

ENEMA (liquid composition for rectal or enteral administration)

$CaCO_3$ 1000 mg
Methylparahydroxybenzoate 40 mg
Propylparahydroxybenzoate 10 mg
Hydrochloric acid ad pH 7.5
Demineralized water q.s. 50 g

We claim:

1. A composition for oral administration comprising a physiologically acceptable coating which is insoluble in gastric juice of pH below 4 and soluble in intestinal juice having a pH from 4 to 7, and a physiologically acceptable pH regulating alkaline material confined within said coating, said pH regulating alkaline material being substantially insoluble, the nature and the amount of said coating and of said pH regulating alkaline material being adapted so as to ensure the availability of an amount of said pH regulating alkaline material in the lumen of a target part of the gastrointestinal tract from the proximal small intestine to the rectum, said target part exhibiting a pH below the pH normally found in said target part, and to ensure a raise in the pH in said lumen to a pH which is close to the pH normally found in said target part.

2. A composition according to claim 1, wherein the target part is a part which by one or more intraluminal pH-measurements has shown pH values below the pH value normally found in said target part.

3. A composition according to claim 1 which is adapted to raise the pH to a pH within the 5–95 percentiles of the normal pH values in said target part of the gastrointestinal tract.

4. A composition according to claim 1 wherein the target part exhibiting a pH below the pH normally found, is the proximal small intestine, the mid small intestine, the distal small intestine, the caecum, the ascending colon, the transverse colon, the descending colon, the sigmoid colon and/or the rectum.

5. A composition according to claim 1 wherein said coating enables the pH regulating alkaline material to pass through the ventricle substantially without being affected by the gastric juices.

6. A composition according to claim 1 wherein the coating is an enterocoating.

7. A composition according to claim 1 wherein the coating is soluble in intestinal juice having a pH from 6 to 7.

8. A composition according to claim 1 wherein the coating is Eudragit L12,5 P.

9. A composition according to claim 1 wherein the pH regulating alkaline material is an acid soluble salt.

10. A composition according to claim 1 wherein the pH regulating alkaline material is soluble in intestinal fluids at a pH below about 5.

11. A composition according to claim 1 wherein the pH regulating alkaline material is selected from the group consisting of substantially insoluble carbonates, silicates, hydroxides and phosphates, preferably of an alkaline earth metal, more preferably calcium or magnesium, most preferably calcium.

12. A composition according to claim 11 wherein the pH regulating alkaline material is calcium carbonate.

13. A composition according to claim 1 wherein the unit dosage of alkaline material ranges from 1 mmol to 1 mol, preferably 5 mmol to 100 mmol, optionally administered 4–6 times per day.

14. A composition according to claim 1 wherein the pH raise is more than ½ unit, optionally 1 or 2 pH units.

15. A composition according to claim 1 wherein the pH regulating alkaline material administered per day is capable of neutralizing from 1–100 milliequivalents acid, preferably 10–60 milliequivalents acids.

16. A composition according to claim 1 wherein the pH regulating alkaline material is in the form of a coated granulate.

17. A composition according to claim 1 wherein the target part exhibiting a pH below the normal pH is the site of a disease afflicting the bowel.

18. A composition according to claim 17 wherein the disease is an invasive bowel disease.

19. A composition according to claim 17 wherein the disease is an inflammatory bowel disease.

20. A composition according to claim 19 wherein the disease is Crohn's disease, colitis ulcerosa or an unclassified form of said diseases.

21. A composition according to claim 17 wherein the disease is a bowel disease microbially induced, e.g., by bacteria such as Salmonella, Campylobacter, Shigella, *E. Coli, Clostridium difficile*, or parasites such as *Entamoeba histolytica*, or vira such as Parvovirus.

22. A composition according to claim 17 wherein the disease is a medicamentally induced bowel disease, e.g., induced by a non-steroid anti-inflammatory drug (NSAID).

23. A composition for the treatment of bowel diseases by oral administration comprising a first physiologically acceptable coating which is insoluble in gastric juice of a pH below 4 and soluble in intestinal juice having a pH from 4 to 7, and a physiologically acceptable pH regulating alkaline material confined within said first coating, said pH regulating alkaline material being substantially insoluble, the nature and the amount of said coating and of said pH regulating alkaline material being adapted so as to ensure the availability of an amount of said pH regulating alkaline material in the lumen of a target part of the gastrointestinal tract from the proximal small intestine to the rectum, said target part exhibiting a pH below the pH normally found in said target part and to ensure a raise in the pH in said lumen to a pH which is close to the pH normally found in said target part, a second physiologically acceptable coating, and an ingredient confined within said second coating, said ingredient being therapeutically active against said bowel disease.

24. A composition according to claim 23 wherein the coated pH regulating alkaline material and the coated active ingredient are each formulated as granulates.

25. A composition according to claim 24 wherein the granulates are filled into a physiologically acceptable capsule.

26. A composition according to claim 24 wherein the granulates are suspending in a liquid.

27. A composition according to claim 23 wherein the active ingredient is a medicament which is selected from an anti-inflammatory medicament, e.g., 5-aminosalicylic acid, 4-aminosalicylic acid, glucocorticoids such as prednisolone for systemic or topic administration; a membrane stabilizing medicament such as disodiumcromoglycate; an immunomodulating/immunosuppressive medicament such as ciclosporin, fucidin, FK506, azathioprine, or 6-mercaptopurine; a cytoprotective or mucosal protective agent such as sucralfate, or bismuth subcitrate; a cytostatic agent such as methotrexate.

28. A composition according to claim 23 wherein the active ingredient is a medicament for treatment of an inflammatory bowel disease.

29. A composition according to claim 28 wherein the inflammatory bowel disease is Crohn's disease, colitis ulcerosa or an unclassifiable form of said diseases.

30. A composition according to claim 28 wherein the active ingredient is 5-aminosalicylic acid or a physiologically acceptable salt or ester thereof.

31. A composition according to claim 23 wherein the active ingredient is a medicament for treatment of microbially induced bowel diseases, e.g., induced by bacteria such as Salmonella, Campylobacter, Shigella, *E. Coli, Clostridium difficile*, or parasites such as *Entamoeba histolytica*, or vira such as Parvovirus.

32. A composition for rectal or enteral administration comprising a physiologically acceptable carrier and a physiologically acceptable pH regulating alkaline material, said pH regulating alkaline material being substantially insoluble, the nature and the amount of said carrier and of said pH regulating alkaline material being adapted so as to ensure the availability of an amount of said pH regulating alkaline material in the lumen of a target part of the colon and/or the rectum, said target part exhibiting a pH below the pH normally found in said target part, and to ensure a raise in the pH in said lumen to a pH which is close to the pH normally found in said target part.

33. A composition according to claim 32 which is formulated as an enema.

34. A composition according to claim 32 which is formulated as suppositories.

35. A composition according to claim 32 wherein the target part is the site of a disease afflicting the lower bowel, e.g., proctitis, protosigmoiditis and/or distal colitis.

36. A method for the treatment of individuals exhibiting a subnormal pH in a target part of the proximal small intestine, the distal small intestine, the caecum, the ascending colon, the transverse colon, the descending colon, the sigmoid colon and/or the rectum, which method comprises administering a substantially insoluble pH regulating alkaline material in a sufficient amount to ensure a raise in the pH in said target part to a pH close to the pH normally found in said target part.

37. A method for adjusting the pH and optionally treating bowel diseases locally in a target part of the gastrointestinal tract comprising the proximal small intestine, the mid small intestine, the distal small intestine, the caecum, the ascending colon, the transverse colon, the descending colon, the sigmoid colon and/or the rectum from a pH value below the normal pH value to a pH value closer to said normal pH value, which method comprises measuring the intraluminal pH in said target part, and administering a composition according to claim 23 whereby said alkaline material is administered in a sufficient amount to ensure a raise in the pH in said target part to a pH close to the pH normally found in said target part and said therapeutically active ingredient is administered in a therapeutically effective amount.

38. A method for adjusting the pH and optionally treating bowel diseases locally in a target part of the gastrointestinal tract comprising the proximal small intestine, the mid small intestine, the distal small intestine, the caecum, the ascending colon, the transverse colon, the descending colon, the sigmoid colon and/or the rectum from a pH value below the normal pH value to a pH value closer to said normal pH value, which method comprises measuring the intraluminal pH in said target part, and administering a composition according to claim 32 whereby said alkaline material is administered in a sufficient amount to ensure a raise in the pH in said target part to a pH close to the pH normally found in said target part and said therapeutically active ingredient is administered in a therapeutically effective amount.

* * * * *